United States Patent [19]

Evans et al.

[11] Patent Number: 5,536,497
[45] Date of Patent: Jul. 16, 1996

[54] FIMBRIAL POLYPEPTIDES USEFUL IN THE PREVENTION OF PERIODONTITIS

[75] Inventors: Richard T. Evans, East Amherst, N.Y.; Gurrinder S. Bedi, Bluebell, Pa.; Robert J. Genco; Hakimuddin T. Sojar, both of Buffalo, N.Y.

[73] Assignee: The Research Foundation of State University of New York, Buffalo, N.Y.

[21] Appl. No.: 994,277

[22] Filed: Dec. 21, 1992

[51] Int. Cl.$^6$ .......................... A61K 39/02; A61K 39/00; A61K 37/02; C07K 14/00
[52] U.S. Cl. ........................ 424/242.1; 424/184.1; 424/185.1; 530/300; 530/326
[58] Field of Search .................. 424/88, 92, 400, 424/401, 242.1, 184.1, 185.1; 530/350, 324, 325, 326, 327, 328, 329, 330

[56] References Cited

U.S. PATENT DOCUMENTS

| | | | |
|---|---|---|---|
| 4,659,561 | 4/1987 | Fives-Taylor et al. | 424/88 |
| 4,661,350 | 4/1987 | Tsurumizo et al. | 424/92 |
| 4,689,221 | 8/1987 | Kiyoshige et al. | 424/87 |
| 4,888,170 | 12/1989 | Curtiss, III | 424/93 |

FOREIGN PATENT DOCUMENTS

| | | |
|---|---|---|
| 61-140527 | 6/1986 | Japan. |
| 12331 | 8/1991 | WIPO. |

OTHER PUBLICATIONS

Dickinson et al (1988) "Molecular Cloning & Sequencing . . ." J. Bact. 170:1658–1665.
Sojar et al (1991) "Purification, Characterization . . ." Biochem. Biophys. Res. Comm. 175:713–719.
Lee et al (1991) "*Porphyromonas (Bacteroides) gingualis* . . ." Inf. Immun. 59:383–389.
Genco et al (1992) "Influence of Immunization . . ." Inf. Immun. 60:1447–1454.
Evans et al, Infect & Immun. 60:2938–2935 1992.
Lee et al (1992 Apr.) "Synthetic Peptide Analogues . . ." Infect. Immun. 60:1662–1670.
Dickinson, et al., "Molecular Cloning and Sequencing of the Gene Encoding the Fimbrial Subunit Protein of *Bacteroides gingivalis*", Jounral of Bacteriology, vol. 170, No. 4, Apr. 1988, pp. 1658–1665.
Lee, et al., "*Porphyromonas (Bacteriodes) gingivalis* Fimbrillin: Size, Amino–Terminal Sequence, and Antigenic Heterogeneity", Infection and Immunity, vol. 59, No. 1, Jan. 1919, pp. 383–389.

Sojar, et al., "Purification, Characterization and Immunolocalization of Fimbrial Protein from Porphyromonas (Bacteroides) gingivalis", Biochemical and Biophysical Research Communications, vol. 175, No. 2, Mar. 15, 1991, pp. 713–719.

Sharma, et al., "PRC Amplification and Cloning of the *Porphyromonas gingivalis* Fimbrillin Gene", Abstract for AADR Meeting of Mar. 11, 1992.

Evans et al, "*Porphyromonas gingivalis* Fimbrial Peptide Inhibits Periodontal Tissue Destruction in Gnotobiotic Rats", Abstract for LADR Meeting of Jul. 1, 1992.

Lee, et al., "Synthetic Peptides Analougous to the Fimbrillin Sequence Inhibit Adherence to *Porphyromonas gingivalis*", Infection and Immunity, vol. 60, No. 4, Apr. 1992, pp. 1662–1670.

Evans et al., "Immunication With *Porphromonas (Bacteriodes) gingivalis* Fimbriae Protects Against Periodontal Destruction", Infection and Immunity, vol. 60, No. 7, Jul.. 1992 pp. 2926–2935.

Evans et al., "Immunication with Fimbrial Protein and Peptide Protects Against *Porphuromonas gingivalis*–Induced Periodontal Tissue Destruction", In Genetically Engineered Vaccines; Prospects For Oral Disease Prevention, Eds. J. A. Ciardy, J. R. McGhee, & J. Keith, Plenum Publishing, Nov. 1992.

*Primary Examiner*—Hazel F. Sidberry
*Attorney, Agent, or Firm*—Hodgson, Russ, Andrews, Woods & Goodyear

[57] ABSTRACT

Polypeptides related to fimbriae of *Porphyromonas gingivalis* are described and claimed which exhibit inhibition of bacterial adhesion to saliva-coated surfaces. The polypeptides are selected from the group consisting of fimbriae, fimbrillin, and fimbrial-related. peptides derived therefrom. The polypeptides are used as active ingredients in various oral formulations designed to prevent adhesion of *P. gingivalis* to host mucosal surfaces and thus interfering with the development of periodontitis. The polypeptides are also used in subunit vaccine formulations for use against pathogenic, fimbriated *P. gingivalis* in the prophylactic treatment of periodontitis. Use of the polypeptides for inducing protective immunity in serum and gingival crevicular fluid may prevent primary infection with *P. gingivalis* as well as the spread of the organism between intraoral reservoirs.

15 Claims, 10 Drawing Sheets

FIMBRIAL POLYPEPTIDES USEFUL IN THE PREVENTION OF PERIODONTITIS

This invention was made in part with government support under grants DE08240, DE07034, DE04898, and DE06514 awarded by the U.S. Public Health Service. The government has certain rights in the invention.

FIELD OF THE INVENTION

The present invention relates to compositions and methods of preparation of protein, and its component peptides, associated with the cell surface of *Porphyromonas gingivalis*. More particularly, the invention is directed to compositions and methods of preparation of *Porphyromonas gingivalis* fimbriae, fimbrillin, and peptides derived thereof, which may be used in the prophylactic treatment of periodontitis.

BACKGROUND OF THE INVENTION

The Disease, *Porphyromonas gingivalis*, and Disease Process

The tissue affected by periodontitis may include the gingival tissue (gums); periodontal membrane (connective tissue embedded in the cementum and alveolar bone); cementum (mineralized connective tissue covering the roots of the teeth); and the alveolar bone (bone socket). Depending on the progression of the disease, there may occur a destruction of periodontal membranes, alveolar bone loss, and apical migration of the connective tissue attachment. Advanced periodontal disease may result in the formation of periodontal pockets harboring bacterial plaque, and progressive loosening and eventual loss of teeth.

*Porphyromonas gingivalis* is a black-pigmented anaerobe that is considered to be a major pathogenic species of Gram-negative subgingival flora. *P. gingivalis* is associated with several periodontal diseases including adult periodontitis, generalized juvenile periodontitis, periodontal abscesses, and refractory periodontitis. The association between *P. gingivalis* and periodontal disease suggests that components of *P. gingivalis* may be useful in strategies to reduce the incidence, and to prevent the development of periodontal disease caused by this pathogen. Initiation of the disease process and subsequent progression is thought to be dependent on the interaction between host factors and bacterial virulence factors which includes the processes of access to host tissue, adherence and colonization, and mediation of tissue destruction.

In developing compositions which could be used for prophylactic treatment of periodontitis, it would be desirable for the compositions to interfere with the initial stages of the disease process, such as adherence to host mucosal surfaces. *P. gingivalis* adheres to a variety of surfaces including epithelial cell surface receptors, salivary components, and other attached bacteria. Components of *P. gingivalis* thought to be involved in adhesion include fimbriae, vesicles, and hemagglutinins. Fimbrial protein of *P. gingivalis* has been purified which facilitates the study of the role of fimbriae in adhesion (Sojar et al., 1991, Biochem. Biophys. Res. Commun. 175:713–719, hereby incorporated by reference). A 43 kilodalton (kDa) protein has been purified from *P. gingivalis* and has been shown to be a major fimbrillin monomer subunit of fimbriae. Studies using different strains of *P. gingivalis*, obtained from a wide geographic distribution, showed immunological cross-reactivity as well as strain-specific antigens (Lee et al., 1991, Infect. Immun. 59:383–389). Although these studies suggest that there is some antigenic conservation among strains of fimbriated *P. gingivalis*, it was not known whether the conserved antigens are important in a host immune response protective against the bacteria, and/or constitute domains which function in adherence by the bacteria.

SUMMARY AND OBJECTS OF THE INVENTION

The present invention is directed to fimbriae, fimbrillin which is a 43 kDa monomeric structural subunit of fimbriae, and peptides derived thereof, of *P. gingivalis*. The fimbrial-related peptides and proteins of the present invention inhibit the binding of different strains of *P. gingivalis* cells to salivary components. The fimbrial-related peptides and proteins may also induce protective antibody in serum, saliva, and gingival crevicular fluid, and/or cellular immune responses which can prevent primary infection with *P. gingivalis* as well as the spread of the organism between intraoral reservoirs.

One object of the present invention is to provide a composition having one or more fimbrial-related peptides and proteins as an active ingredient of an oral rinse designed to prevent adhesion of *P. gingivalis* to host mucosal surfaces and thus interfering with the development of periodontitis.

Another object of the present invention is to provide such a composition which may be incorporated into other formulations such as dentifrices or topical agents.

Another object of the present invention is to provide a composition having one or more fimbrial-related peptides and proteins as immunogens in a subunit vaccine formulation for use against all pathogenic, fimbriated *P. gingivalis* in the prophylactic treatment of periodontitis.

In accordance with the method of the present invention, fimbrial-related peptides and proteins for oral application or subunit vaccine preparations can be obtained by chemical synthesis, purification from *P. gingivalis*, or purification from recombinant expression systems.

BRIEF DESCRIPTION OF THE FIGURES

FIG. 2 graphically illustrates binding assays to investigate the role of adherence of *P. gingivalis* to saliva.

FIG. 6 is a graphic illustration of the inhibitory effect of smaller fimbrial-related peptides on the binding of *P. gingivalis* to sHAP beads.

FIG. 7 is a graphic illustration of analysis for bone loss and of bone support in germ free animals (GF); animals infected with P. gingivalis (IF); and infected animals previously immunized with either heat-killed whole cells (WC), the 43 kDa protein (43), peptide (P), or peptide plus carrier (P+C).

FIG. 8 is a graphic illustration showing results of gingival tissue proteolytic enzyme activity in germ free animals (GF); animals infected with P. gingivalis (IF); and infected animals previously immunized with either heat-killed whole cells (WC), the 43 kDa protein (43), peptide (P), or peptide plus carrier (P+C).

DETAILED DESCRIPTION OF THE INVENTION

Figure 1:
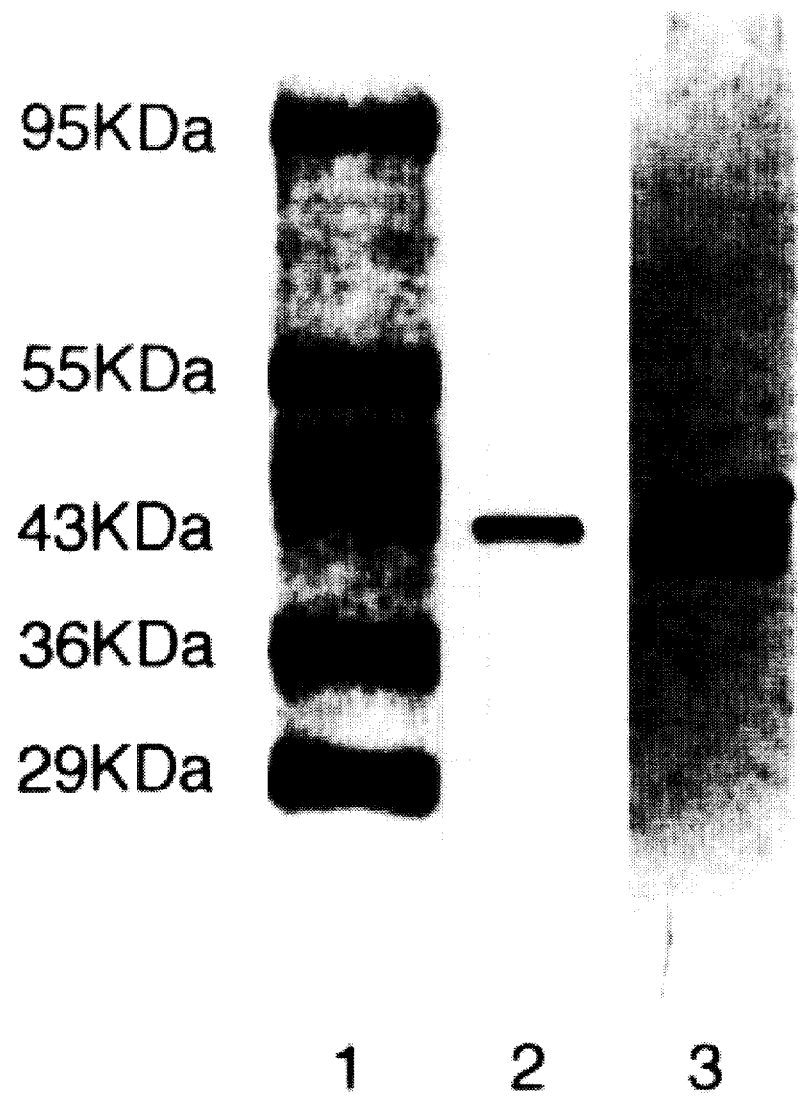
FIG. 1 represents SDS-PAGE analysis (lane 2) and Western blot analysis (lane 3) of the purified 43 kDa fimbrial component. The molecular weight standards are noted in lane 1.

The present invention is directed to fimbrillin, a 43 kDa monomer subunit; peptides derived thereof; and fimbriae, polymers of repeated fimbrillin monomer subunits, of P. gingivalis. For purposes of illustration only, the fimbrillin is referred to as a 43 kDa protein, although it is understood that the molecular size of fimbrillin is in the range of from about 41 kDa to about 49 kDa, depending on the strain serving as the source for fimbrial purification. Fimbriae, and fimbrillin preparations may be obtained from cultures of P. gingivalis by means of shearing or mild sonication of a bacterial cell suspension. Fimbrial-related peptides may be chemically synthesized or derived by proteolytic digestion of fimbriae or fimbrillin preparations.

In one embodiment of the present invention, fimbrial-related peptides and proteins are used as the active ingredient in an oral rinse, dentifrice, topical agent, or other oral formulation to inhibit the binding of different strains of P. gingivalis cells to saliva-coated surfaces. Alternatively, a nonpathogenic species of the microbial flora of the oral mucosal surfaces may be genetically engineered to produce P. gingivalis fimbrial-related peptides, thus serving as a continuous, localized source of inhibiting peptides. Further, somatic gene transfer of fimbrial-related peptides and proteins into, for example, cells of the salivary gland or oral mucous membrane, may be used to protect individuals.

In another embodiment of the present invention peptides and proteins may be used as immunogens in various synthetic or natural vaccine formulations to protect against infection with P. gingivalis. Inducing protective antibody in serum and gingival crevicular fluid may prevent primary infection with P. gingivalis as well as the spread of the organism between intraoral reservoirs. Antibodies induced by immunization with fimbrial-related peptides and proteins may disrupt the disease process by one or more of the following mechanisms: inhibition of bacterial adherence to salivary-coated oral surfaces; inhibition of the growth of the bacteria subgingivally; stimulation of immune cells against the bacteria; and inhibition of fimbrial-mediated stimulation of host destructive factors. As an alternative to a subunit vaccine formulation, the nucleic acid sequence encoding fimbrillin, or peptides thereof, may be incorporated into a live virus vaccine preparation to provide a continual source of induction of mucosal immunity. Further, somatic gene transfer of fimbrial-related peptides and proteins into, for example, cells of the salivary gland, may be used to immunize individuals.

For the purposes of description, the method of the invention will be broken down into the following examples and embodiments:

1) Purification of P. gingivalis fimbriae and isolation of fimbrillin; 2) Physico-chemical analysis of fimbrillin; 3) Synthesis of fimbrial-related peptides; 4) Binding and inhibition of binding of P. gingivalis to saliva-coated surfaces by fimbrillin and related peptides; 5) Induction of protective antibody and/or cellular immunity against P. gingivalis with fimbrillin and fimbrial-related peptides; 6) Vaccine formulations against P. gingivalis; and 7) Oral compositions for the prevention of periodontal disease due to P. gingivalis.

EXAMPLE I

Purification of P. gingivalis fimbriae to homogeneity was an important step for studying the role of these structures in microbial adhesion, and as vaccine candidates. Fimbrillin was purified using the method of Sojar et al. (1991, Biochem. Biophys. Res. Commun. 175:713–719). Cultures of P. gingivalis were harvested by centrifugation and washed with a 50 mM Tris-Cl pH 8.0 buffer containing 10% sucrose, and 1 mM of protease inhibitor PMSF. The cell pellet was suspended in the same buffer and fimbriae were sheared from the cells by mild sonication with a 3 mm microtip using a 20 W pulse setting with a 50% duty cycle in a Vibra cell model VC 250 sonicator. Unbroken, whole cells were removed from the sonicate by centrifugation at 10,000×g for 15 minutes in a Sorvall RC 5C centrifuge. An additional centrifugation, at 100,000×g for one hour in a Beckman LS8-80 ultracentrifuge, resulted in a supernatant containing mainly the 43 kDa fimbrillin protein, and an outer membrane protein of 75 kDa. The supernatant was dialyzed overnight against 50 mM Tris-Cl buffer at pH 8.0. SDS and $MgCl_2$ was added to the dialyzed solution bringing final concentrations to 1% SDS and. 0.2M $MgCl_2$. The pH was adjusted to 6.5 with 1 M HCl and the mixture was stirred continuously overnight at 4° C. The precipitated proteins were collected by centrifugation at 10,000×g for 30 minutes, dissolved in a small volume of 50 mM Tris buffer at pH 8.0, and dialyzed against the same buffer. The clear supernatant was readjusted to pH 6.5 with 1M HCL and the precipitation step was repeated 3 to 4 times to obtain purified 43 kDa fimbrillin protein free of the 75 kDa component. SDS was removed from the 43 kDa protein by passage through a column containing EXTRACTI-GEL D (Pierce Manufacturing Company) previously equilibrated with 50 mM Tris-Cl pH 8.0.

The homogeneity of the purified 43 kDa protein is shown in FIG. 1, lane 2, as a single band on a silver-stained SDS-polyacrylamide gel. The purified 43 kDa protein showed a ladder-like pattern when the sample was heated to 80° in preparation for SDS PAGE, and could be dissociated into its monomeric form only after heating at 100° C. for 10 minutes. Homogeneity was also confirmed by Western blot analysis wherein only a single band at 43 kDa was observed when tested with antisera developed to whole *P. gingivalis* (FIG. 1, lane 2).

EXAMPLE II

The identity of the 43 kDa protein was confirmed by physicochemical analysis as fimbrillin. First the amino acid composition of the protein was determined. The amino acid content matched the deduced composition obtained from the clone fimbrillin gene of Dickinson et al. (1988,J. Bacteriol. 170:1658–1665). Secondly, the sequence of the first thirty residues of the purified 43 kDa protein, elucidated by automated Edman degradation, was consistent with the predicted sequence of the cloned fimbrillin gene referred to above. Finally, the fimbrial nature of the 43 kDA protein was confirmed by electron microscopy using immunogold labelling of both purified 43 kDa protein and *P. gingivalis* cells with antibodies specific for the 43 kDa protein.

EXAMPLE III

The fimbrial-related peptides (Table 1), used in accordance with the method of the present invention, correspond to the amino acid sequence derived from the DNA sequence of the cloned fimbrillin gene of Dickinson et al. (1988,J. Bacteriol. 170:1658–1665). Different strains of *P. gingivalis* have been divided into groups based on their immunoreactivity with various anti-fimbriae, and anti-fimbrial peptide antibodies, and on the basis of amino-terminal sequence analysis (Lee et al., 1991, Infection and Immunity 59:383–389). Sequence analysis of representative strains of the each of the *P. gingivalis* fimbrial major groups show that although there is some differences in amino acid sequence, the differences are not evident in the amino acid sequence from which the peptides of the present invention are derived.

Peptide synthesis can be performed using one of the following procedures:

1) Peptide synthesis can be performed by a solid-phase technique using tertiary butyl oxycarbonyl (t-Boc)-protected amino acids and the t-butoxycarbonyl-4-methyl-benzyl-L-cysteinephenylacetamidomethyl resin substituted to the extent of 0.22 mmol/g as the solid support. Synthesis was performed in a peptide synthesizer, and the peptide chains were assembled by using a double-coupling program. At the end of the program for each amino acid, a sample of resin was removed and tested for completion of coupling by the Kaiser ninhydrin test. The peptides were cleaved from the resin with simultaneous removal of the side chain-protecting groups by treatment with hydrogen fluoride for 1 hour at 0° C. in the presence of anisole. The peptide-resin mixture was washed four times with anhydrous ether to remove anisole, and the peptides were extracted with 5% acetic acid and lyophilized. The crude peptides were purified using high-pressure liquid chromatography (HPLC) on an RP-18 column and amino acid sequence analysis was performed to establish purity and to confirm sequence.

2) Alternatively, synthetic peptides can be prepared using a solid-phase Fmoc (9-fluoroenylmethoxycarbonyl) peptide synthesis procedure with a peptide synthesizer. Briefly, the carboxyl-terminal amino acid was coupled to the 4-hydroxymethylphenoxymethyl copolystyrene-1% divinyl benzene resin by using N,N'-dicyclohexylcarbodiimide as an activating reagent and 0.1 dimethylaminopyridine in N,N'-dimethylformamide as a catalyst. The α-amino group of the amino acid was protected by an Fmoc group which was subsequently deprotected at the beginning of every cycle by the addition of 20% piperidine. The carboxyl group of the subsequent amino acids was activated by the 1-hydroxybenzotrazole-N-N'-dicyclohexylcarbodiimide activation method and mixed with the deprotected amino terminal of the growing peptide chain. Cleavage of the peptides from the resin was performed by using 95% trifluoroacetic acid- 5% thioanisol as a scavenger. Cleaved peptides were precipitated with diethylether and lyophilized. Peptides may be purified using HPLC, and amino acid sequence analysis may be performed to establish purity and to confirm sequence.

3) Some of the synthetic peptides may be digested with proteolytic enzymes to obtain fragments comprising smaller peptides. For example, peptide 226–245 was trypsinized to obtain smaller peptides 226–236, and 240–245, by dissolving 20 mg of HPLC-purified peptide 226–245 in 3 ml of 0.5 ammonium bicarbonate buffer,pH 5.6 and incubating for 10 hours at room temperature with 400 μg of trypsin-tosyl-L-phenylalanyl chromethyl ketone (TPCK). After the 10 hour incubation, the mixture was further incubated overnight at room temperature with an additional 300 μg of trypsin-TPCK. After lyophilization, the peptide was dissolved in 0.1% TFA-H$_2$O, centrifuged, and the supernatant was subjected to HPLC to separate out individual peptides resulting from the proteolytic digestion.

TABLE I

FIMBRIAL-RELATED PEPTIDES

| Residue No. | Sequence |
| --- | --- |
| 49–68[a] | Val Val Met Ala Asn Thr Gly Ala Met Glu Leu Val Gly Lys Thr Leu Ala Glu Val Lys -c |
| 126–146 | Arg Met Ala Phe Thr Glu Ile Lys Val Gln Met Ser Ala Ala Tyr Asp Asn Ile Tyr Thr Phe |
| 186–205 | Tyr Thr Pro Ala Asn Tyr Ala Asn Val Pro Trp Leu Ser Arg Asn Tyr Val Ala Pro Ala |
| 226–245 | Ile His Pro Thr Ile Leu Cys Val Tyr Gly Lys Leu Gln Lys Asn Gly Ala Asp Leu Ala |
| 226–236 | Ile His Pro Thr Ile Leu Cys Val Tyr Gly Lys |
| 240–245 | Asn Gly Ala Asp Leu Ala |
| 266–286 | Tyr Pro Val Leu Val Asn Phe Asn Ser Asn Asn Tyr Thr Tyr Asp Ser Asn Tyr Thr Pro Lys |
| 293–306 | His Lys Tyr Asp Ile Lys Leu Thr Ile Thr Gly Pro Gly Thr |
| 293–300 | His Lys Tyr Asp Ile Lys Leu Thr |
| 300–306 | Thr Ile Thr Gly Pro Gly Thr |
| 307–326 | Asn Asn Pro Glu Asn Pro Ile Thr Glu Ser Ala His Leu Asn Val Gln Cys Thr Val Ala |
| 318–337 | His Leu Asn Val Gln Cys Thr Val Ala Glu Trp Val Leu Val Gly Gln Asn Ala Thr Trp |

[a]synthesized using tertiary butyl oxycarbonyl-protected amino acids (-c).

EXAMPLE IV

1. Binding assays:

To investigate the role of fimbriae in adherence of *P. gingivalis* to saliva, binding assays were developed (Lee et al., 1992, Infect. Immun. 60:1662–1670, hereby incorporated by reference). Clarified whole human saliva was prepared by collecting saliva, centrifuging it at 10,000×g for 10 minutes, heating the saliva at 60° C. for 30 minutes to inactivate endogenous enzymes, and centrifuging at 12,000×g for 15 minutes to remove precipitated materials. The clarified human saliva was used to coat spherical hydroxyapatite (HAP) beads by first washing the beads, in a siliconized borosilicate culture tube, with distilled water, and then equilibrating the beads in a rotator at room temperature overnight in buffered KCl containing 0.04% NaN$_3$. The HAP beads were then washed twice with buffered KCL treated with clarified whole human saliva containing 0.04% NaN$_3$ in a rotator at room temperature overnight, and then washed twice with buffered KCl.

Figure 2A:
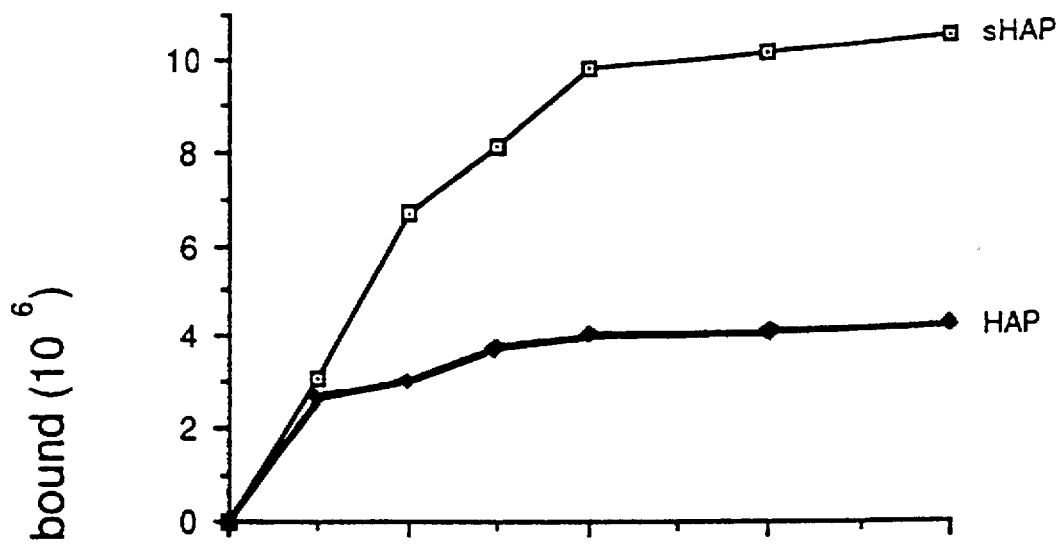
FIG. 2a is a binding curve of $^3$H-labelled *P. gingivalis* strain 2561 to buffered KCl-treated hydroxyapatite (HAP) and saliva-coated hydroxyapatite (sHAP) beads.
Figure 2B:
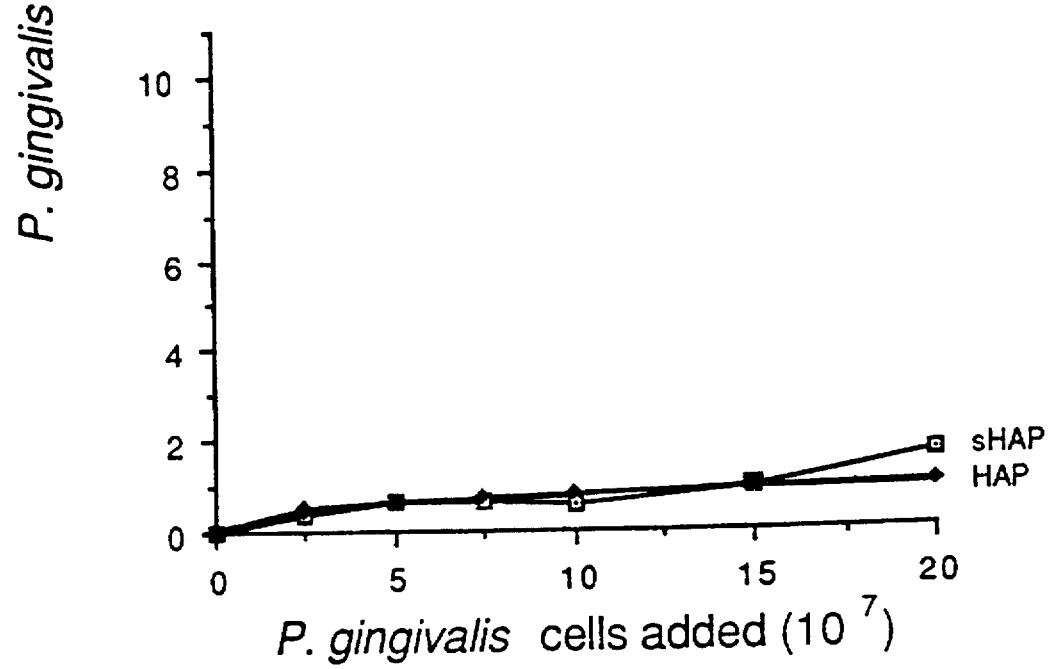
FIG. 2b is a binding curve of $^3$H-labelled *P. gingivalis* strain W50 to buffered KCl-treated HAP and sHAP beads.

In preparation for the binding assay, strains of P. gingivalis were radiolabelled during growth by incubating the cells in [$^3$H] thymidine at 37° C. for 2 days in an anaerobic chamber. The strains used include a fimbriated strain (2561) and a non- or poorly fimbriated strain (W50). P. gingivalis binding to saliva-coated HAP (sHAP) beads was compared with binding to HAP beads equilibrated with buffered KCl. A concentration-dependent binding curve was obtained by adding 2.5×10$^7$ to 2×10$^8$ $^3$H-labelled P. gingivalis cells to 2 mg of HAP or sHAP beads. The binding assay was performed by incubating the cells with the beads in tubes containing a final volume of 400 μl with buffered KCl. The tubes were incubated for 1 hour on a rotator at 20 rpm to agitate the contents to disperse aggregates and to maximize binding of P. gingivalis cells. Following the incubation, the mixture was layered on 1.5 ml of 100%. PERCOLL in a new siliconized tube to separate P. gingivalis cells which were free from those bound to beads. Unbound cells floating on the PERCOLL layer were removed by aspiration. The beads with bound cells were washed once with. 0.5 ml PERCOLL, twice with 1 ml of buffered KCl and then placed in a vial for quantitation of radioactivity. At a saturation level of 10$^8$ cells, P. gingivalis 2561 cells binding to sHAP beads was 2.5 times greater than binding to HAP. As shown in FIG. 2a, approximately 10% of P. gingivalis 2561 bound to sHAP beads, whereas 4% bound to HAP beads. Non- or poorly fimbriated strain W50 exhibited only low leveling binding to sHAP and HAP beads (FIG. 2b). Taken together, these two observations suggest that P. gingivalis fimbriae are involved in adhesion to saliva-coated surfaces.

Figure 3:
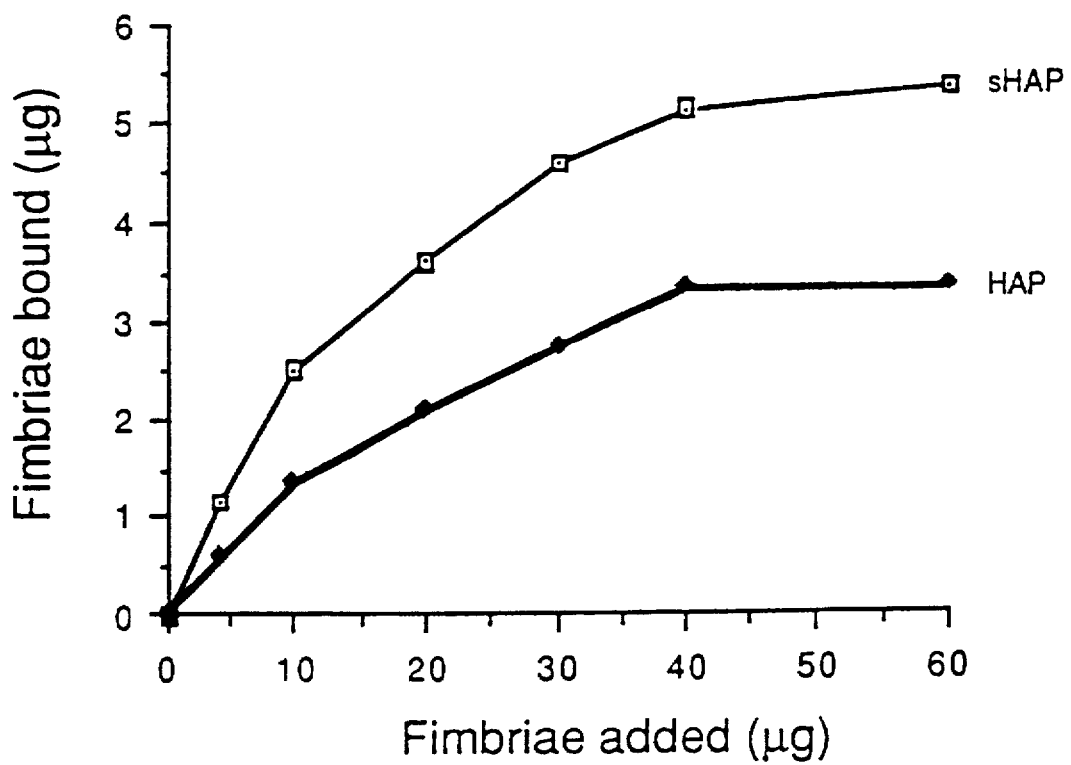
FIG. 3 graphically illustrates binding curves of $^{125}$I-labelled purified fimbriae to HAP and sHAP beads.

For a fimbria binding assay, fimbriae were purified as previously discussed, and radiolabelled by iodination using a modification of the chloramine T method. A working solution of iodinated fimbriae (0.4 mg/ml) was prepared in buffered KCl. The fimbria binding assay was performed in the same manner as the whole cell binding assay described above, except that 10 to 150 ul of the iodinated fimbrial preparation was added to HAP or sHAP beads, bringing the final volume to 200 μl with buffered KCl. As shown in FIG. 3, purified labelled fimbriae also bound to sHAP beads in a concentration-dependent manner and reached a saturation level when approximately 40 μg of fimbriae was added to 50 mg of sHAP beads. Demonstration of direct binding of purified fimbriae to sHAP beads is further evidence suggesting a role for fimbriae in binding of P. gingivalis cells to salivary components.

2. Inhibition Assays

Figure 4:
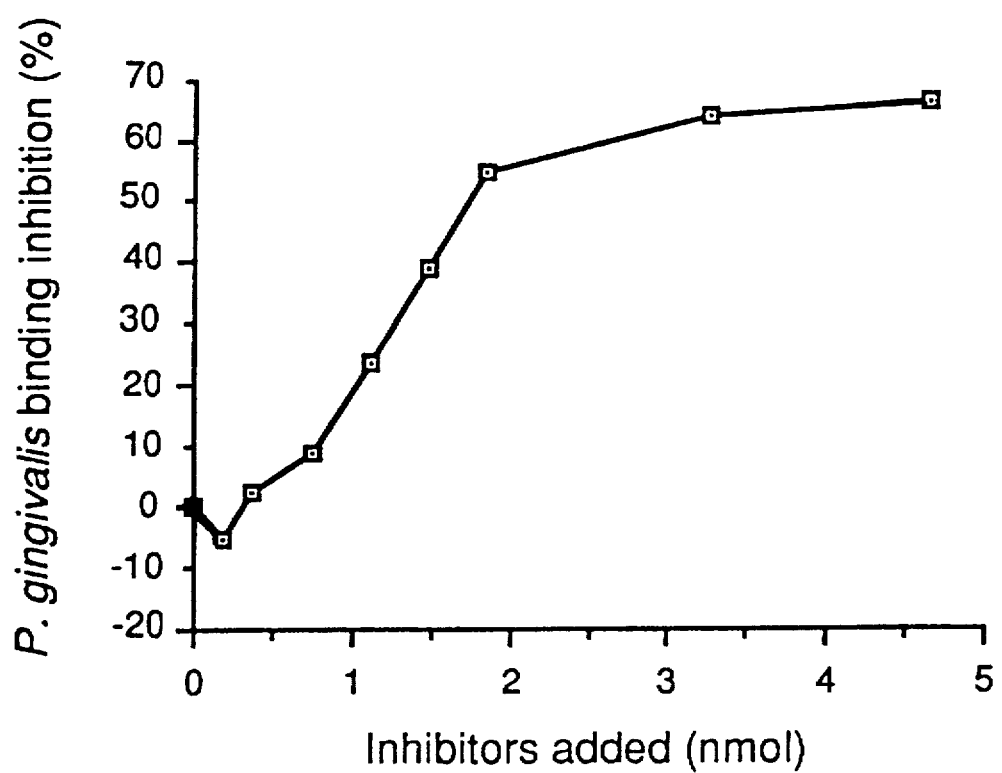
FIG. 4 is a graphic illustration of the inhibition curve of purified fimbriae on the binding of *P. gingivalis* to sHAP beads.

To further characterize the role of fimbriae in binding of P. gingivalis cells to salivary components, purified fimbriae and fimbrial-related peptides were tested for their ability to inhibit P. gingivalis whole cell binding to sHAP beads. The peptides also served as a tool for localizing active binding domains of fimbrillin to sHAP beads. For inhibition of P. gingivalis binding to sHAP beads by fimbriae, the beads (2 mg) were incubated with radiolabelled P. gingivalis 2561 (300 μl of a suspension of 4×10$^8$ cells/ml) in the presence of increasing concentrations of the purified fimbriae (8 to 200 μg). P. gingivalis binding to sHAP beads was inhibited by 65% when 200 μg of fimbriae was added (FIG. 4).

Figure 5:
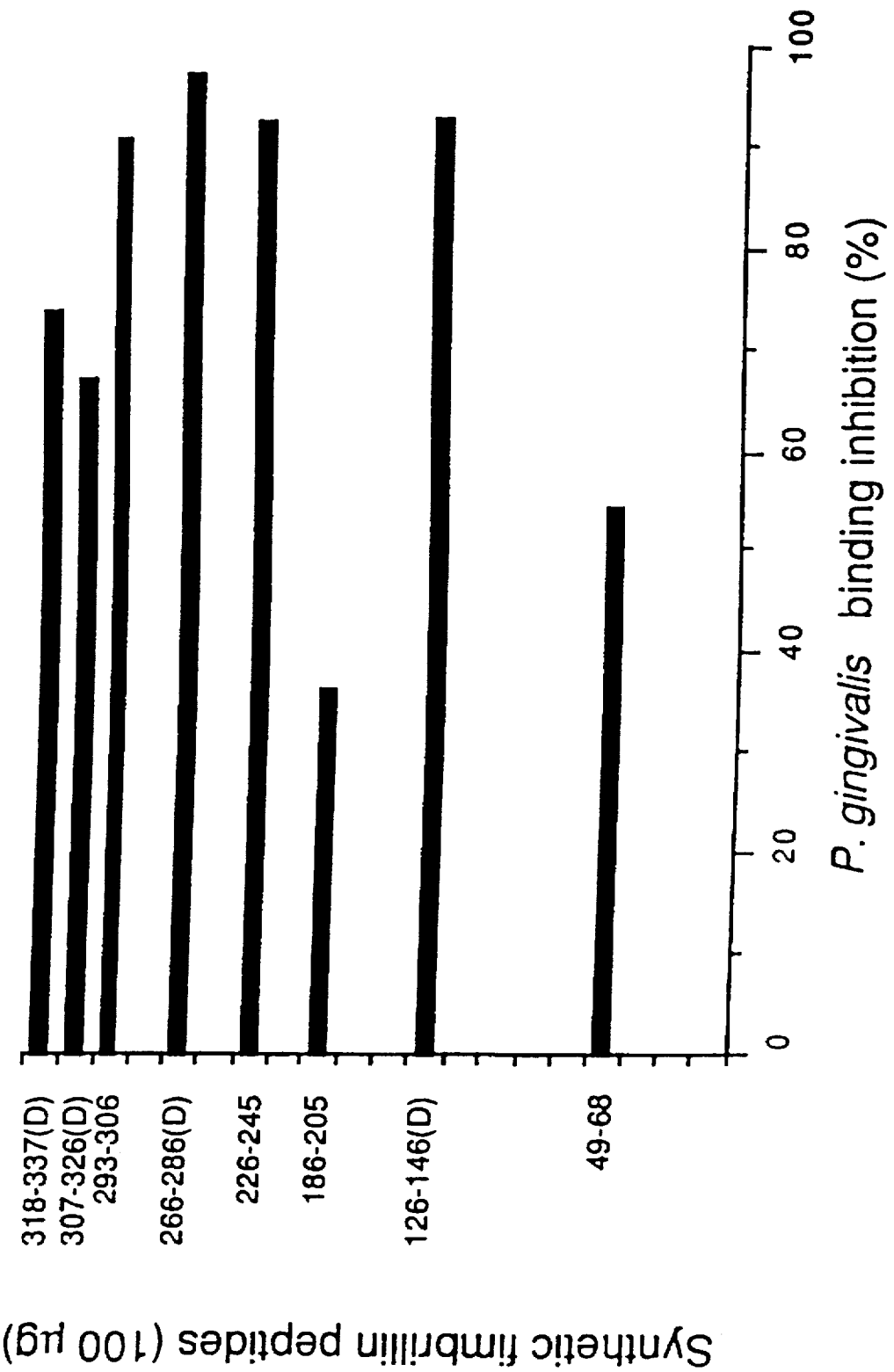
FIG. 5 is a graphic illustration of the inhibitory effect of synthetic fimbrial-related peptides on the binding of *P. gingivalis* to sHAP beads.
Figure 6A:
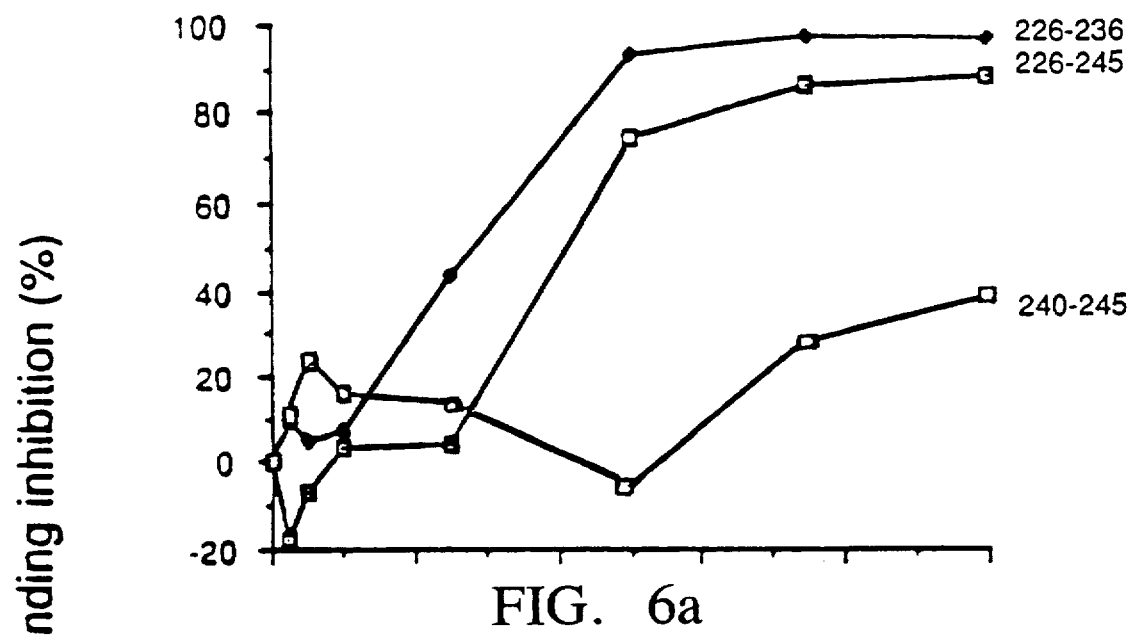
FIG. 6a and graphically illustrates the inhibitory effect of peptide derivatives of the peptide 226–245.
Figure 6B:
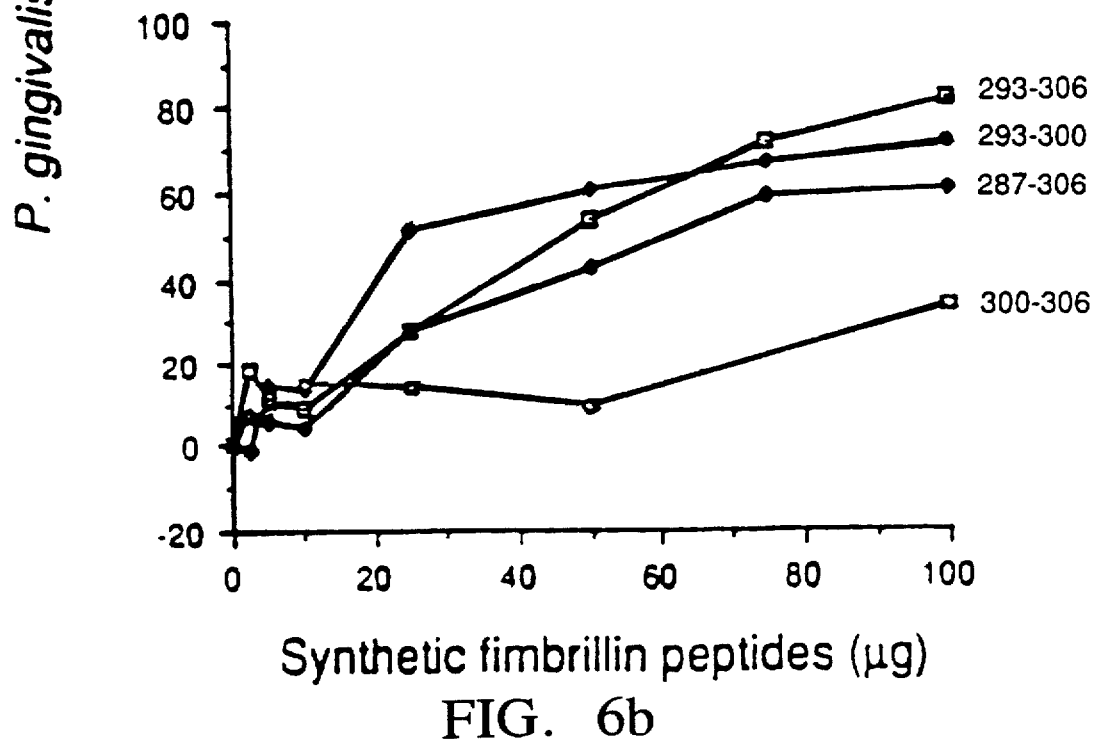
FIG. 6b graphically illustrates the inhibitory effect of peptide derivatives of the peptide 287–306.

The ability of the fimbrial-related peptides to inhibit the binding of P. gingivalis was tested in reaction mixtures containing 2 mg of sHAP beads incubated with 300 μl of P. gingivalis (of a suspension containing 4×10$^8$ cells/ml) and 100 μl (100 μg) of each peptide. One peptide derived from the amino-terminal sequence of fimbrillin (peptide 126–145), and several peptides from the carboxy-terminal one-third of fimbrillin (peptides 226–245, 266–288, 293–306, 307–326, and 318–337 ) exhibited strong inhibition ranging from 70 to 95% as shown in FIG. 5. The inhibition by these peptides of P. gingivalis binding to sHAP beads was concentration-dependent. One of the smaller peptides (226–236) derived from peptide 226–245, showed a very strong inhibitory effect on binding of P. gingivalis to sHAP beads, whereas the other smaller peptide (240–245) showed weak inhibition (FIG. 6a). Similarly, the inhibitory effect of smaller peptide 293–300 was comparable to that of the parental peptide 293–306, whereas the other smaller peptide, 300–306, showed a low binding inhibition effect (FIG. 6b).

3. Effect of various agents on binding of P. gingivalis to sHAP beads

To better understand the nature of the noncovalent interactions involved in P. gingivalis binding to sHAP beads, and with relevance to the compatibility of different agents as co-ingredients with fimbrillin or fimbrial-related peptides in an oral composition for preventing the development of periodontal disease due to P. gingivalis, various agents were tested for their effects on binding (Table 2). Calcium ions, charged amino acids, neutral sugars, N-acetyl hexosamines, neuraminidase, and protease inhibitors had little or no effect on P. gingivalis binding. Poly-L-lysine, BSA, and defatted BSA at high concentrations exhibited an inhibitory effect ranging from 36 to 43% on P. gingivalis binding to sHAP beads. D-glucuronic acid, D-galacturonic acid, and sialic acid inhibited binding by 21 to 33%. Pretreatment of sHAP beads with trypsin or α-chymotrypsin prior to being mixed with P. gingivalis cells reduced the binding by approximately 50%.

TABLE 2

EFFECT OF VARIOUS AGENTS ON P. gingivalis BINDING

| Agents | Amount/ conc. | Inhibition (%) |
| --- | --- | --- |
| Buffered KCl (1 mM CaCl$_2$) | | 0 |
| Buffered KCl (EGTA treated)* | | 5 |
| Buffered KCl with 5 mM CaCl$_2$ | | 1 |
| L-Arginine | 0.1 mg | 0 |
| L-Lysine | 0.1 mg | 5 |
| Poly-L-lysine | 0.25 mg | 41 |
| BSA | 1 mg | 36 |
| Defatted BSA | 1 mg | 43 |
| D-Galacturonic acid | 0.1 mg | 21 |
| D-Glucuronic acid | 0.1 mg | 33 |
| Sialic acid (N-acetyl neuraminic acid) | 0.1 mg | 28 |
| N-Acetyl neuramin-lactose | 0.1 mg | 2 |
| Colominic acid (poly-2,8-N-acetyl neuraminic acid) | 0.1 mg | 13 |
| N-Acetylgalactosamine | 0.1 mg | −5 |
| N-Acetylglucosamine | 0.1 mg | −15 |
| Galactosamine | 0.1 mg | 8 |
| Glucosamine | 0.1 mg | 0 |
| Fucose | 0.1 mg | 1 |
| Galactose | 0.1 mg | −7 |
| Glucose | 0.1 mg | −10 |
| Mannose | 0.1 mg | −15 |
| Lactose | 0.1 mg | −1 |
| Maltose | 0.1 mg | −8 |

TABLE 2-continued

EFFECT OF VARIOUS AGENTS ON P. gingivalis BINDING

| Agents | Amount/conc. | Inhibition (%) |
| --- | --- | --- |
| EDTA | 1 mM | 24 |
| Leupeptin | 2 µM | 19 |
| Pepstatin | 1 µM | −10 |
| 1,10-Phenanthroline | 1 mM | −8 |
| Phenylmethylsulfonyl fluoride | 2 mM | 13 |
| Trypsin, bovine pancreas type XIII-TPCK | 100 U | 53 |
| α-Chymotrypsin, bovine pancreas type VII-TLCK | 0.5 U | 52 |
| Neuraminidase, *Clostridium perfringens* type V | 5 mU | 21 |

*EGTA is ethylene glycol-bis(B-aminoethyl ether)-N,N,N',N'-tetraacetic acid.
**A minus number indicates enhancement of *P. gingivalis* 2561 binding to sHAP beads.

EXAMPLE V

Fimbrillin and fimbrial-related peptides may be used in accordance with the present invention as antigens to induce protective immunity against *P. gingivalis*. Immunization with the purified 43 kDa protein and with a 20 amino acid fimbrial-related peptide was compared to immunization with whole cells in reducing *P. gingivalis* induced periodontal bone loss in an animal model for primate periodontal disease.

1. Animal model for vaccination studies

An animal model useful for immunization studies was developed utilizing rats because of their similarity, with respect to humans, in periodontal anatomy, microbiology, and pathogenesis of periodontal disease (Evans et al., 1992, Infection and Immunity, 60:2926–2935). The duration of the infective process of *P. gingivalis* in rats is sufficient to detect periodontal bone loss. Periodontal tissue destruction may be estimated by measuring alveolar bone loss morphometically and radiographically. Suppression of gingival tissue proteolytic enzyme activities, particularly collagenase, cathepsin B & L, and gelatinase, may be used as indicia of the inhibition of gingival tissue destruction.

2. Fimbrial antigens

Antigens were prepared from *P. gingivalis* strains 381 and the genetically identical strain 2561 (also called ATCC strain 33277). Heat-killed *P. gingivalis* whole cell antigen was made by heating strain 381 at 60° C. for 15 minutes on two successive days. The 43 kDa fimbrillin subunit was purified using the method previously described herein. The synthetic peptide, peptide 226–245 (see Table 1), was prepared using the F moc peptide synthesis procedure previously described herein.

3. Immunization protocol

Rats were immunized twice, subcutaneously, one week apart in Freund's incomplete adjuvant. Immunizations using peptide were done with peptide alone for one group of animals, and peptide conjugated with thyroglobulin as a carrier for another group. Antibody concentrations were measured using a particle concentration immunofluorescence assay wherein the concentration is expressed in terms of relative fluorescence units (RFU). Animals were infected on three alternate days with viable cells of *P. gingivalis* strain 381 in 1 ml of 5% low viscosity carbomethylcellulose one week following immunization. The animals were evaluated for alveolar bone loss approximately 42 days following the initial infection.

Figure 7A:
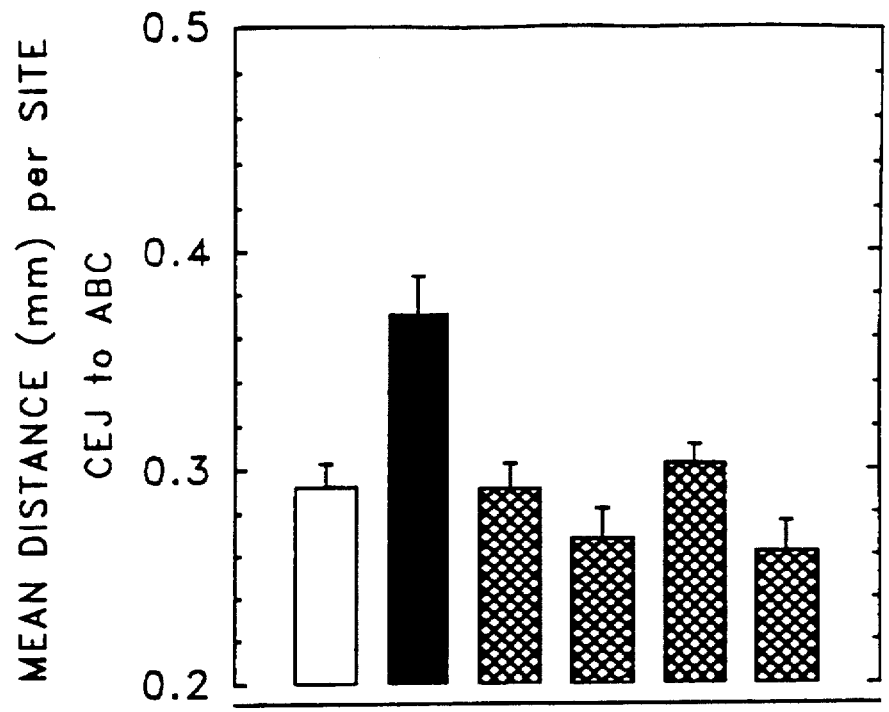
FIG. 7a illustrates the bone loss analysis.

The horizontal bone level changes were evaluated in immunized and infected animals as shown in FIG. 7a. Germfree (GF) rats which were both sham-immunized and sham-infected served as a baseline control. Sham-immunized animals (IF), and carrier-immunized animals (C) infected with *P. gingivalis* strain 381, served as positive controls showing significant periodontal disease and bone loss. Infected animals protected against bone loss include those immunized with heat-killed whole cells (WC); those immunized with the 43 kDa fimbrillin subunit (43); those immunized with peptide alone (P); and those immunized with peptide-carrier conjugate (P+C).

Figure 7B:
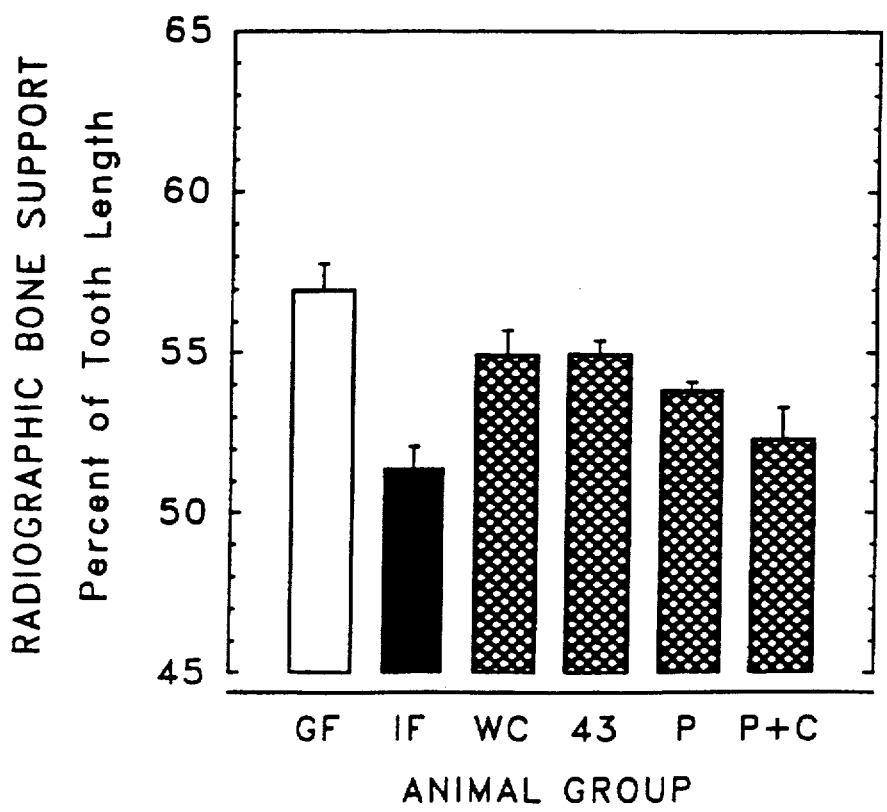
FIG. 7b illustrates bone support analysis.

Vertical intrabony lesions in the mandible, expressed as percent bone support, was measured using the radiographic technique. As shown in FIG. 7b, the fimbrillin (43) and the whole cell (WC) immunized animals had bone support comparable to the GF animals, whereas animals immunized with peptide (P) or peptide conjugated to carrier (P+C) showed less protection.

Figure 8A:
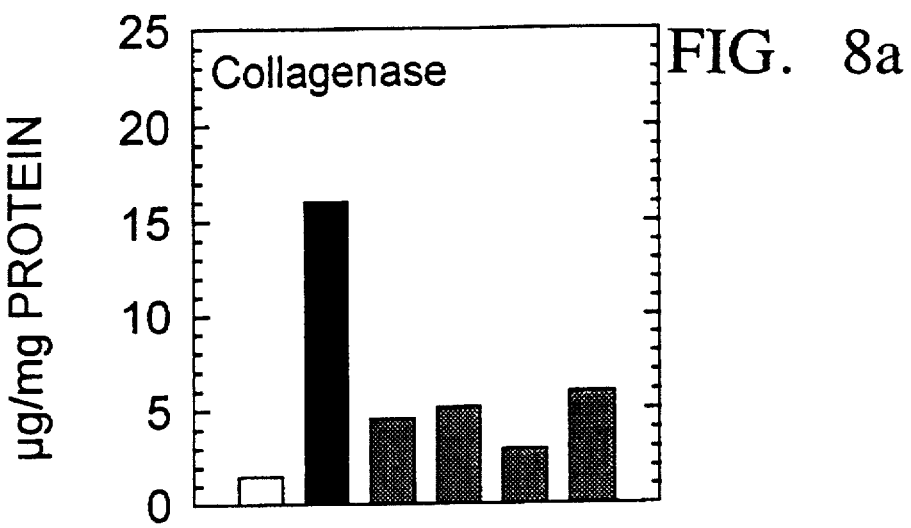
FIG. 8a illustrates the level of collagenase activity.
Figure 8B:
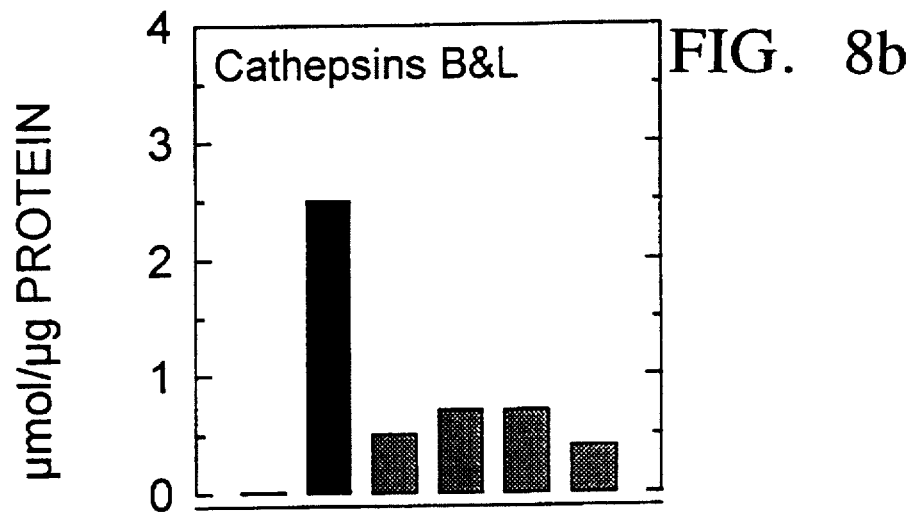
FIG. 8b illustrates the level of cathepsins activity.
Figure 8C:
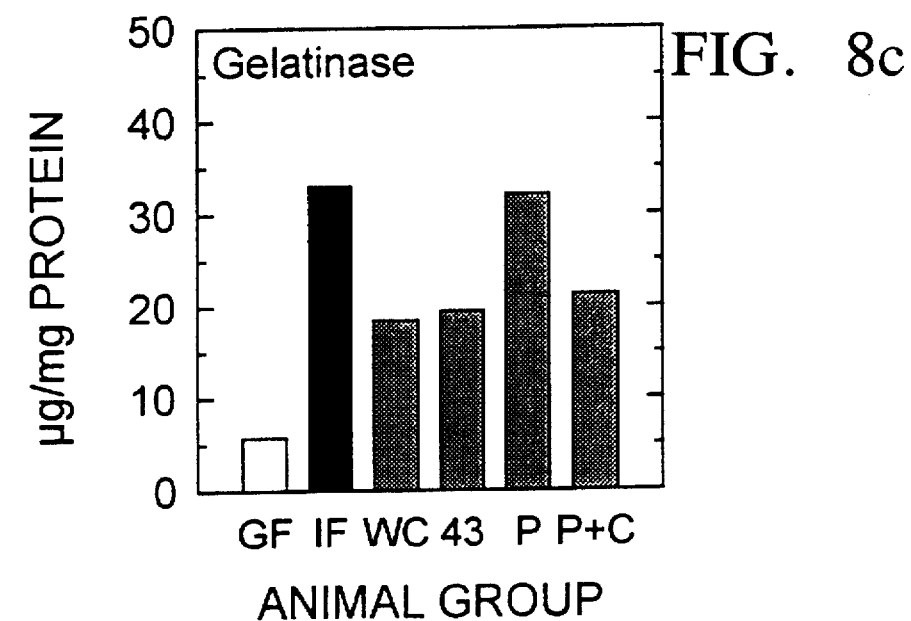
FIG. 8c illustrates the level of gelatinase activity.

Examination of gingival tissue for proteolytic enzyme activity (FIG. 8) revealed highly elevated levels of collagenase (FIGS. 8a), cathepsin B & L (FIG. 8b), and gelatinase (FIG. 8c) in the strain 381 infected rats (IF). Animals immunized with whole cells (WC), fimbrillin (43), peptide (P), or peptide with carrier (P+C) showed significantly reduced levels of proteolytic activity (FIG. 8).

Figure 9:
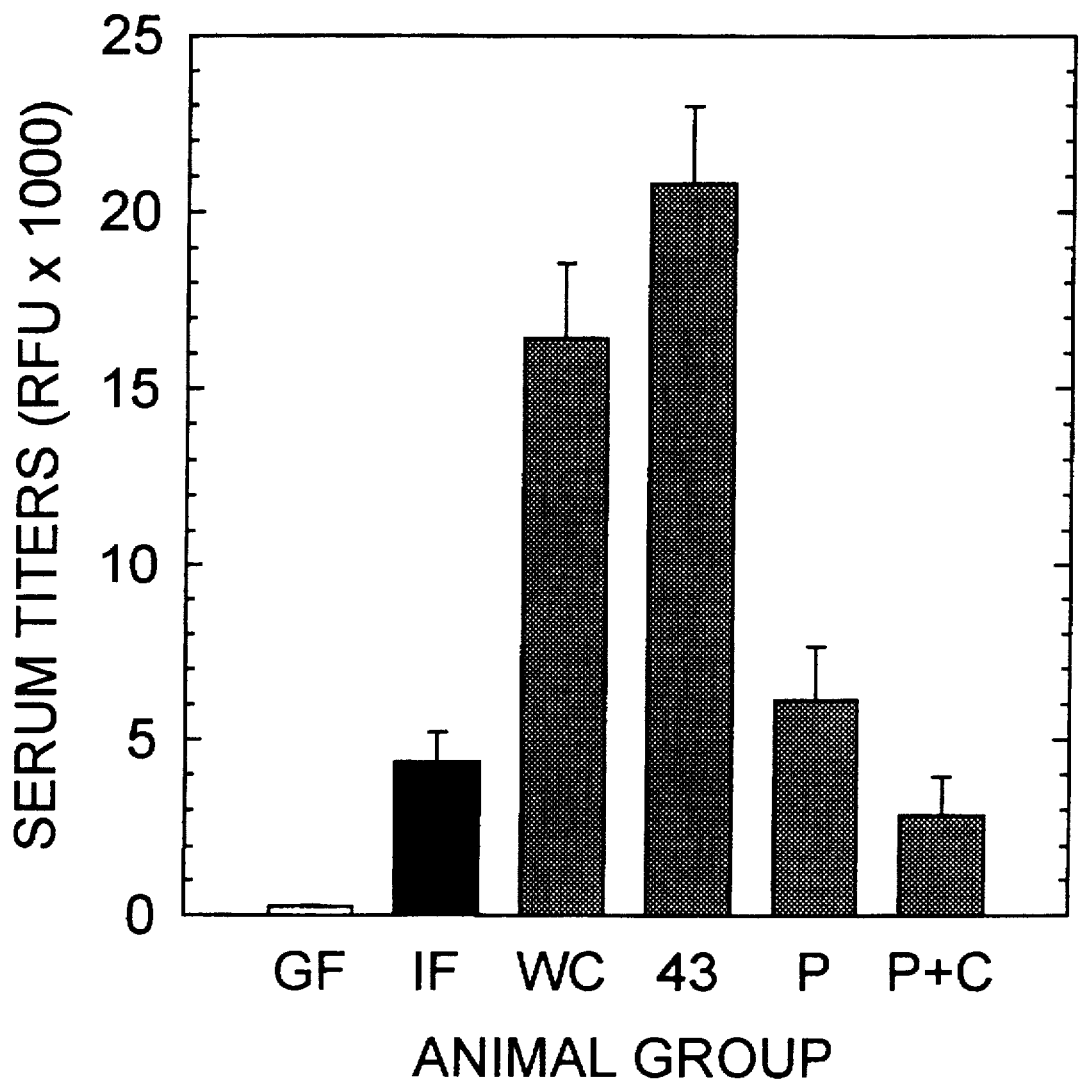
FIG. 9 is a graphic illustration of serum antibody measurements to the 43 kDa fimbrial component in germ free animals (GF); animals infected with P. gingivalis (IF); and infected animals previously immunized with either heat-killed whole cells (WC), the 43 kDa protein (43), peptide (P), or peptide plus carrier (P+C).
Figure 10:
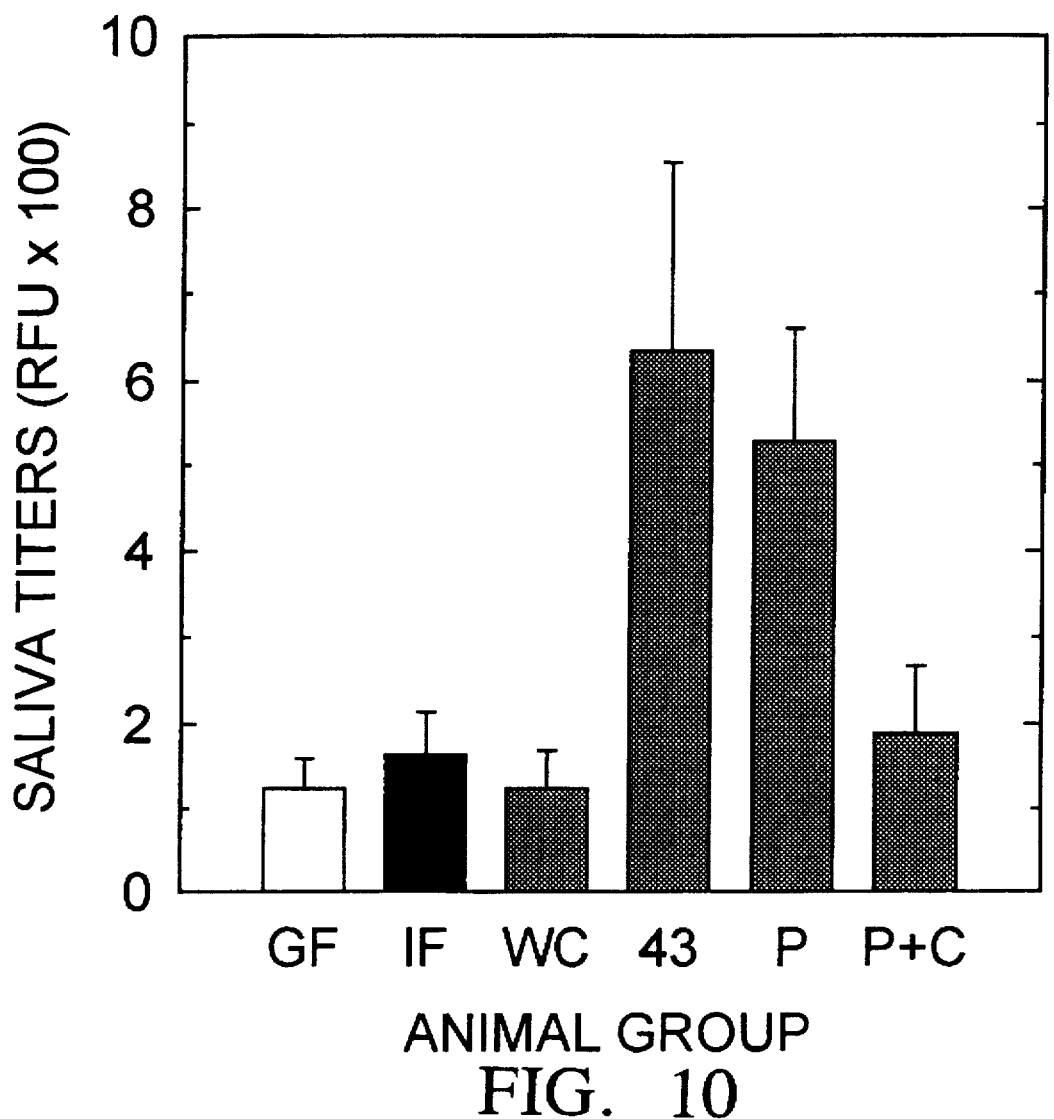
FIG. 10 is a graphic illustration of salivary antibody measurements to the 43 kDa fimbrial component in germ free animals (GF); animals infected with P. gingivalis (IF); and infected animals previously immunized with either heat-killed whole cells (WC), the 43 kDa protein (43), peptide (P), or peptide plus carrier (P+C).

Immunization with whole cells (WC), fimbrillin (43), and peptide (P) increased both serum (FIG. 9) and salivary (FIG. 10) antibody titers when tested against the 43 kDa fimbrial component. Deliberate vaccination of animals with fimbrial antigens produced a greater immune response than that induced in animals following infection (IF) with *P. gingivalis*.

In summary, evidence of the effectiveness of fimbrial antigens as a component of an vaccine effective against *P. gingivalis* includes induction of a significant anti-fimbrial antibody response; suppression of gingival proteolytic enzyme activities induced by infection; and protection against bone loss indicative of infection.

EXAMPLE VI

1. Vaccine Formulations

The vaccine formulations, in accordance with the present invention, may be introduced by any one of several routes of administration known in the art which include, but are not limited to: subcutaneous, intravenous, intramuscular, intradermal, intraperitoneal, intranasal, intraoral. One embodiment of the present invention is to provide proteins or peptides related to fimbrillin of *P. gingivalis* which may be used as immunogens in various synthetic or natural vaccine formulations to protect against infection with *P. gingivalis*. A subunit vaccine may comprise solely fimbrillin which is isolated in substantially pure form from cultures of fimbriated strains of *P. gingivalis*. Alternatively, genetically engineered fimbrillin, from recombinant organisms expressing the fimbrillin gene, may be purified for use as the immunogenic material of a vaccine. Similarly, fimbrial-related peptides may be chemically synthesized, or derived using protease digestion of purified fimbrillin from *P. gingivalis* or of recombinant origin. Whether the protein or related peptide is isolated from recombinant organisms, or from *P. gingivalis*, or chemically synthesized, the purified fimbrillin and/or fimbrial-related peptides may be mixed in appropriate concentration with a physiological solution with or without an additional ingredient comprising a suitable vaccine adjuvant selected from those known in the art. Also the fimbrillin and/or fimbrial-related peptides may be incorporated into any one of the drug delivery mechanisms known in the art such as liposomes, or by conjugation to biocompatible polymers.

Another embodiment of the present invention is to provide proteins or peptides related to fimbrillin of *P. gingivalis* which may be used as immunogens in a recombinant viral vaccine to protect against infection with *P. gingivalis*. A recombinant viral vaccine may be constructed by using conventional methods for inserting DNA encoding fimbrillin, or fimbrial-related epitopes (i.e. of one or more peptides in Table 1) into genetic material to be introduced into or incorporated into a virus or virus-like particle known in the art as suitable for vaccination purposes. A live recombinant viral vaccine may be preferred because multiplication of the recombinant virus in the human host may lead to prolonged or continual stimulation of the host protective immune response to fimbrial-related antigens. Vaccinia virus is an example of such a virus which can be genetically engineered to produce fimbrial-related antigens to be introduced into a human host for vaccine purposes.

Yet another embodiment of the present invention is somatic gene transfer of fimbrillin or fimbrial-related peptides. "Somatic gene transfer", as a term used throughout this specification and the appended claims, is intended to cover any and all methods comprising the introduction of a vector into a host cell, wherein the vector is a nucleic acid construct containing the nucleic acid sequence encoding fimbrillin, and/or a nucleic acid sequence encoding a portion thereof (one or more fimbrial-related peptides). The introduction of the nucleic acid construct into host cells may be accomplished by any one of several methods known in the art including, without limitation, transformation, transfection, microinjection, $CaPO_4$ precipitation, electroporation, targeted liposomes, particle-guar bombardment, and electrofusion. The host cells may include blood or bone marrow cells, or cells of the salivary gland or oral mucous membrane. Depending on the origin of host cell and the method for introduction of the vector, the host cell may either be removed from, treated, and re-introduced back into the individual; or introduction of the vector into host cells of the individual may be accomplished in-situ. As as example of the former, bone marrow cells may +be removed from an individual, wherein the cells are cultured in-vitro and transformed with the nucleic acid construct, followed by re-introduction of the transformed cells by injection into the circulatory system of the individual where the cells migrate to become re-established in the bone marrow tissue. As an example of the latter, transformation of cells of the salivary gland or oral mucous membrane can be accomplished in-situ by encapsulating constructs of the present invention into liposomes using established methods, binding commercially available antibodies to the surface of the liposomes which specifically bind to cells of the salivary gland or oral mucous membrane, and using these engineered liposomes as a component in a rinse to allow them to come into intimate contact with these target cells where the liposomes will bind and subsequently be absorbed into these cells. The vector may be either a plasmid or retrovirus in which the nucleic acid construct directs transcription, within the host cell, to the respective RNA corresponding to fimbrillin and/or fimbrial-related peptide(s). Thus, somatic gene transfer is a method, in accordance with the present invention, whereby cells of an individual may be genetically engineered to produce fimbrial-related peptides and proteins which may be a source of continual antigenic stimulation for immunization of that individual; or to produce a continual source of fimbrial-related peptides and proteins which may protect individuals by inhibiting the binding of *P. gingivalis* to saliva-coated surfaces.

EXAMPLE VII

1. Oral Formulations

In another embodiment of the present invention, fimbrial-related peptides and proteins are used singly or in combination as the active ingredient in an oral rinse, dentifrice, topical agent, or other oral formulation to inhibit the binding of different strains of *P. gingivalis* cells to saliva-coated surfaces. As described for the vaccine formulations, fimbrial protein or related peptide may be isolated from recombinant organisms, or from *P. gingivalis*, or be chemically synthesized. The purified fimbrillin and/or fimbrial-related peptides may be mixed in appropriate concentration with a solution comprising one or more agents which act as an effective pharmaceutical carrier or base. The solution may vary in composition depending on the application of the oral formulation, i.e if the composition is to be utilized as an oral rinse, dentifrice, or topical agent. Table 2 may serve as a guide for choosing different agents to be incorporated into a solution for use as compatible co-ingredients with fimbrillin or fimbrial-related peptides in an oral composition for preventing the development of periodontal disease due to *P. gingivalis*. It is within the scope of the present invention to add a conventional dye or other suitable additive to color and/or add taste to the oral formulation.

Alternatively, an oral formulation may contain as an active ingredient a sufficient number of a nonpathogenic species of the microbial flora for colonization of the oral mucosal surfaces, wherein the species of microbial flora has been genetically engineered to produce *P. gingivalis* fimbrial-related peptides. Such a recombinant microorganism may be constructed by using conventional methods for inserting a vector containing DNA encoding fimbrial-related peptides into the microorganism for expression of the peptides. The peptides may be one or more peptides selected from Table 1. A microorganism normally residing in the oral flora may be preferred because multiplication of the recombinant microorganism expressing fimbrial-related peptides in the human host's oral cavity may serve as a continuous, localized source of inhibiting peptides. An additional benefit may be that the peptides produced locally may serve as a source of antigen which could also stimulate a localized immune response against *P. gingivalis*.

It should be understood that while the invention has been described in detail herein, the examples were for illustrative purposes only, and the invention can be embodied otherwise without departing from the principles thereof. Such other embodiments are meant to come within the scope of the present invention as defined by the appended claims.

---

What is claimed is:

1. An isolated and purified peptide that inhibits *P. gingivalis* adhesion to a saliva-coated surface, said peptide consists of an amino acid sequence selected from the group consisting of:

| | |
|---|---|
| SEQ ID No:1- | Val Val Met Ala Asn Thr Gly Ala Met Glu Leu Val Gly Lys Thr Leu Ala Glu Val Lys; |
| SEQ ID No:2- | Arg Met Ala Phe Thr Glu Ile Lys Val Gln Met Ser Ala Ala Tyr Asp Asn Ile Tyr Thr Phe; |
| SEQ ID No:3- | Tyr Thr Pro Ala Asn Tyr Ala Asn Val Pro Trp Leu Ser Arg Asn Tyr Val Ala Pro Ala; |
| SEQ ID No:4- | Ile His Pro Thr Ile Leu Cys Val Tyr Gly Lys Leu Gln Lys Asn Gly Ala Asp Leu Ala; |
| SEQ ID No:5- | Ile His Pro Thr Ile Leu Cys Val Tyr Gly Lys; |
| SEQ ID No:6- | Asn Gly Ala Asp Leu Ala; |
| SEQ ID No:7- | Tyr Pro Val Leu Val Asn Phe Asn Ser Asn Asn Tyr Thr Tyr Asp Ser Asn Tyr Thr Pro Lys; |
| SEQ ID No:8- | His Lys Tyr Asp Ile Lys Leu Thr Ile Thr Gly Pro Gly Thr; |
| SEQ ID No.:9- | His Lys Tyr Asp Ile Lys Leu Thr; |
| SEQ ID No.:10- | Thr Ile Thr Gly Pro Gly Thr; |
| SEQ ID No.:11- | Asn Asn Pro Glu Asn Pro Ile Thr Glu Ser Ala His Leu Asn Val Gln Cys Thr Val Ala; and |
| SEQ ID No:12- | His Leu Asn Val Gln Cys Thr Val Ala Glu Trp Val Leu Val Gly Gln Asn Ala Thr Trp. |

2. The peptide of claim 1, wherein the peptide was chemically synthesized.

3. A composition useful in the prevention of periodontitis, said composition contains:

(a) an active ingredient of at least one peptide that inhibits *P. gingivalis* adhesion to a saliva-coated surface, said peptide is an isolated and purified peptide consisting of an amino acid sequence selected from the group consisting of:

| | |
|---|---|
| SEQ ID No:1- | Val Val Met Ala Asn Thr Gly Ala Met Glu Leu Val Gly Lys Thr Leu Ala Glu Val Lys; |
| SEQ ID No:2- | Arg Met Ala Phe Thr Glu Ile Lys Val Gln Met Ser Ala Ala Tyr Asp Asn Ile Tyr Thr Phe; |
| SEQ ID No:3- | Tyr Thr Pro Ala Asn Tyr Ala Asn Val Pro Trp Leu Ser Arg Asn Tyr Val Ala Pro Ala; |
| SEQ ID No:4- | Ile His Pro Thr Ile Leu Cys Val Tyr Gly Lys Leu Gln Lys Asn Gly Ala Asp Leu Ala; |
| SEQ ID No:5- | Ile His Pro Thr Ile Leu Cys Val Tyr Gly Lys; |
| SEQ ID No:6- | Asn Gly Ala Asp Leu Ala; |
| SEQ ID No:7- | Tyr Pro Val Leu Val Asn Phe Asn Ser Asn Asn Tyr Thr Tyr Asp Ser Asn Tyr Thr Pro Lys; |
| SEQ ID No:8- | His Lys Tyr Asp Ile Lys Leu Thr Ile Thr Gly Pro Gly Thr; |
| SEQ ID No.:9- | His Lys Tyr Asp Ile Lys Leu Thr; |
| SEQ ID No.:10- | Thr Ile Thr Gly Pro Gly Thr; |
| SEQ ID No.:11- | Asn Asn Pro Glu Asn Pro Ile Thr Glu Ser Ala His Leu Asn Val Gln Cys Thr Val Ala; and |
| SEQ ID No:12- | His Leu Asn Val Gln Cys Thr Val Ala Glu Trp Val Leu Val Gly Gln Asn Ala Thr Trp; and |

(b) a compatible chemical agent as a carrier or diluent.

4. The composition according to claim 3, wherein the composition is an oral formulation selected from the group consisting of a dentifrice, an oral rinse, and a topical agent.

5. The composition according to claim 3, wherein the peptide was chemically synthesized.

6. A method of preventing periodontitis comprising applying externally to teeth and gum tissues a pharmaceutically effective amount of the composition according to claim 3.

7. The method of claim 6, wherein the pharmaceutically effective amount of the composition is applied as active ingredients in a dentifrice.

8. The method of claim 6, wherein the pharmaceutically effective amount of the composition is applied as active ingredients in an oral rinse.

9. The method of claim 6, wherein the pharmaceutically effective amount of the composition is applied as active ingredients in a topical agent.

10. A vaccine formulation, effective against periodontitis, comprising an immunologically effective amount of a substantially pure peptide that can inhibit *P. gingivalis* adhesion to a saliva-coated surface, said peptide consists of an amino acid sequence selected from the group consisting of:

| | |
|---|---|
| SEQ ID No:1- | Val Val Met Ala Asn Thr Gly Ala Met Glu Leu Val Gly Lys Thr Leu Ala Glu Val Lys; |
| SEQ ID No:2- | Arg Met Ala Phe Thr Glu Ile Lys Val Gln Met Ser Ala Ala Tyr Asp Asn Ile Tyr Thr Phe; |

-continued

SEQ ID No:3- Tyr Thr Pro Ala Asn Tyr Ala Asn Val Pro Trp
Leu Ser Arg Asn Tyr Val Ala Pro Ala;

SEQ ID No:4- Ile His Pro Thr Ile Leu Cys Val Tyr Gly Lys
Leu Gln Lys Asn Gly Ala Asp Leu Ala;

SEQ ID No:5- Ile His Pro Thr Ile Leu Cys Val Tyr Gly Lys;

SEQ ID No:6- Asn Gly Ala Asp Leu Ala;

SEQ ID No:7- Tyr Pro Val Leu Val Asn Phe Asn Ser Asn Asn
Tyr Thr Tyr Asp Ser Asn Tyr Thr Pro Lys;

SEQ ID No:8- His Lys Tyr Asp Ile Lys Leu Thr Ile Thr Gly
Pro Gly Thr;

SEQ ID No.:9- His Lys Tyr Asp Ile Lys Leu Thr;

SEQ ID No.:10- Thr Ile Thr Gly Pro Gly Thr;

SEQ ID No.:11- Asn Asn Pro Glu Asn Pro Ile Thr Glu Ser Ala
His Leu Asn Val Gln Cys Thr Val Ala; and SEQ ID No:12- His Leu Asn Val Gln Cys Thr Val Ala Glu
Trp Val Leu Val Gly Gln Asn Ala Thr Trp.

11. The vaccine formulation according to claim 10, wherein the peptide was chemically synthesized.

12. The vaccine formulation of claim 10, further comprising a physiologically acceptable carrier.

13. A method for protection of a mammal against periodontitis caused by *Porphyromonas gingivalis* comprising administering to a mammal an effective amount of the vaccine formulation according to claim 10.

14. A method for protection of a mammal against periodontitis caused by *Porphyromonas gingivalis* comprising administering to a mammal an effective amount of the vaccine formulation according to claim 11.

15. A method for protection of a mammal against periodontitis caused by *Porphyromonas gingivalis* comprising administering to a mammal an effective amount of the vaccine formulation according to claim 12.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 20 amino acid residues
        ( B ) TYPE: amino acid
        ( C ) TOPOLOGY: linear ( i i ) MOLECULE TYPE:
        ( A ) DESCRIPTION: peptide ( i i i ) HYPOTHETICAL: no ( i v ) FRAGMENT TYPE: N-terminal ( v ) ORIGINAL SOURCE:
        ( A ) ORGANISM: Porphyromonas gingivalis
        ( B ) STRAIN: 381

( v i ) FEATURE:
        ( A ) IDENTIFICATION METHOD: Inhibition Assays
        ( B ) OTHER INFORMATION: inhibits binding of P. gingivalis
            whole cell and fimbriae to salivary components.

( v i i ) PUBLICATION INFORMATION:
        ( A ) AUTHORS: Lee, Jin-Yong; Sojar, Hakimuddin T.; Bedi,
            Gurrinder S.; Genco, Robert J.
        ( B ) TITLE: Synthetic Peptides Analogous to the Fimbrillin
            Sequence Inhibit Adherence of Porphyromonas
            gingivalis
        ( C ) JOURNAL: Infection and Immunity
        ( D ) VOLUME: 60
        ( E ) ISSUE: 4
        ( F ) PAGES: 1662-1670
        ( G ) DATE: April 1992
        ( K ) RELEVANT RESIDUES IN SEQ ID NO: From 49 to 68

( v i i i ) SEQUENCE DESCRIPTION: SEQ ID NO: 1:

```
Val  Val  Met  Ala  Asn  Thr  Gly  Ala  Met  Glu  Leu  Val  Gly  Lys  Thr
 1                  5                        10                       15

Leu  Ala  Glu  Val  Lys
                    20
```

( 2 ) INFORMATION FOR SEQ ID NO:2:

( i ) SEQUENCE CHARACTERISTICS:
        ( A ) LENGTH: 21 amino acid residues
        ( B ) TYPE: amino acid
        ( C ) TOPOLOGY: linear ( i i ) MOLECULE TYPE:
        ( A ) DESCRIPTION: peptide ( i i i ) HYPOTHETICAL: no ( i v ) FRAGMENT TYPE: internal ( v ) PUBLICATION INFORMATION:
        ( A ) RELEVANT RESIDUES IN SEQ ID NO: From 126-146
            (without counting the first 10 amino acids which comprise
        the leader sequence)

( v i ) SEQUENCE DESCRIPTION: SEQ ID NO: 2:

```
Arg  Met  Ala  Phe  Thr  Glu  Ile  Lys  Val  Gln  Met  Ser  Ala  Ala  Tyr
 1                  5                        10                       15

Asp  Asn  Ile  Tyr  Thr  Phe
                    20
```

( 2 ) INFORMATION FOR SEQ ID NO:3:

( i ) SEQUENCE CHARACTERISTICS:
        ( A ) LENGTH: 20 amino acid residues
        ( B ) TYPE: amino acid
        ( C ) TOPOLOGY: linear -continued ( i i ) MOLECULE TYPE:
    ( A ) DESCRIPTION: peptide ( i i i ) HYPOTHETICAL: no ( i v ) FRAGMENT TYPE: internal ( v ) PUBLICATION INFORMATION:
    ( A ) RELEVANT RESIDUES IN SEQ ID NO: From 186-205
        (without counting the first 10 amino acids which comprise the leader sequence)

( v i ) SEQUENCE DESCRIPTION: SEQ ID NO: 3:

Tyr Thr Pro Ala Asn Tyr Ala Asn Val Pro Trp Leu Ser Arg Asn
 1           5                   10                  15
Tyr Val Ala Pro Ala
            20

( 2 ) INFORMATION FOR SEQ ID NO:4:

( i ) SEQUENCE CHARACTERISTICS:
        ( A ) LENGTH: 20 amino acid residues
        ( B ) TYPE: amino acid
        ( C ) TOPOLOGY: linear ( i i ) MOLECULE TYPE:
        ( A ) DESCRIPTION: peptide ( i i i ) HYPOTHETICAL: no ( i v ) FRAGMENT TYPE: internal ( v ) PUBLICATION INFORMATION:
        ( A ) RELEVANT RESIDUES IN SEQ ID NO: From 226-245
            (without counting the first 10 amino acids which comprise the leader sequence)

( v i ) SEQUENCE DESCRIPTION: SEQ ID NO: 4:

Ile His Pro Thr Ile Leu Cys Val Tyr Gly Lys Leu Gln Lys Asn
 1           5                   10                  15
Gly Ala Asp Leu Ala
            20

( 2 ) INFORMATION FOR SEQ ID NO:5:

( i ) SEQUENCE CHARACTERISTICS:
        ( A ) LENGTH: 11 amino acid residues
        ( B ) TYPE: amino acid
        ( C ) TOPOLOGY: linear ( i i ) MOLECULE TYPE:
        ( A ) DESCRIPTION: peptide ( i i i ) HYPOTHETICAL: no ( i v ) FRAGMENT TYPE: internal ( v ) PUBLICATION INFORMATION:
        ( A ) RELEVANT RESIDUES IN SEQ ID NO: From 226-236
            (without counting the first 10 amino acids which comprise the leader sequence)

( v i ) SEQUENCE DESCRIPTION: SEQ ID NO: 5:

Ile His Pro Thr Ile Leu Cys Val Tyr Gly Lys
 1           5               10

( 2 ) INFORMATION FOR SEQ ID NO:6:

( i ) SEQUENCE CHARACTERISTICS:
        ( A ) LENGTH: 6 amino acid residues
        ( B ) TYPE: amino acid ( C ) TOPOLOGY: linear ( i i ) MOLECULE TYPE:
                    ( A ) DESCRIPTION: peptide ( i i i ) HYPOTHETICAL: no ( i v ) FRAGMENT TYPE: internal ( v ) PUBLICATION INFORMATION:
                    ( A ) RELEVANT RESIDUES IN SEQ ID NO: From 240-245
                        (without counting the first 10 amino acids which comprise the leader sequence)

( v i ) SEQUENCE DESCRIPTION: SEQ ID NO: 6:

Asn Gly Ala Asp Leu Ala
 1               5

( 2 ) INFORMATION FOR SEQ ID NO:7:

( i ) SEQUENCE CHARACTERISTICS:
                    ( A ) LENGTH: 21 amino acid residues
                    ( B ) TYPE: amino acid
                    ( C ) TOPOLOGY: linear ( i i ) MOLECULE TYPE:
                    ( A ) DESCRIPTION: peptide ( i i i ) HYPOTHETICAL: no ( i v ) FRAGMENT TYPE: internal ( v ) PUBLICATION INFORMATION:
                    ( A ) RELEVANT RESIDUES IN SEQ ID NO: From 266-286
                        (without counting the first 10 amino acids which comprise the leader sequence)

( v i ) SEQUENCE DESCRIPTION: SEQ ID NO: 7:

Tyr Pro Val Leu Val Asn Phe Asn Ser Asn Asn Tyr Thr Tyr Asp
 1               5                   1 0                 1 5

Ser Asn Tyr Thr Pro Lys
                 2 0

( 2 ) INFORMATION FOR SEQ ID NO:8:

( i ) SEQUENCE CHARACTERISTICS:
                    ( A ) LENGTH: 14 amino acid residues
                    ( B ) TYPE: amino acid
                    ( C ) TOPOLOGY: linear ( i i ) MOLECULE TYPE:
                    ( A ) DESCRIPTION: peptide ( i i i ) HYPOTHETICAL: no ( i v ) FRAGMENT TYPE: internal ( v ) PUBLICATION INFORMATION:
                    ( A ) RELEVANT RESIDUES IN SEQ ID NO: From 293-306
                        (without counting the first 10 amino acids which comprise the leader sequence)

( v i ) SEQUENCE DESCRIPTION: SEQ ID NO: 8:

His Lys Tyr Asp Ile Lys Leu Thr Ile Thr Gly Pro Gly Thr
 1               5                   1 0

( 2 ) INFORMATION FOR SEQ ID NO:9:

( i ) SEQUENCE CHARACTERISTICS:
                    ( A ) LENGTH: 8 amino acid residues
                    ( B ) TYPE: amino acid
                    ( C ) TOPOLOGY: linear ( i i ) MOLECULE TYPE:
    ( A ) DESCRIPTION: peptide ( i i i ) HYPOTHETICAL: no ( i v ) FRAGMENT TYPE: internal ( v ) PUBLICATION INFORMATION:
    ( A ) RELEVANT RESIDUES IN SEQ ID NO: From 293-300
        (without counting the first 10 amino acids which comprise the leader sequence)

( v i ) SEQUENCE DESCRIPTION: SEQ ID NO: 9:

```
His Lys Tyr Asp Ile Lys Leu Thr
 1               5
```

( 2 ) INFORMATION FOR SEQ ID NO:10:

( i ) SEQUENCE CHARACTERISTICS:
        ( A ) LENGTH: 7 amino acid residues
        ( B ) TYPE: amino acid
        ( C ) TOPOLOGY: linear ( i i ) MOLECULE TYPE:
        ( A ) DESCRIPTION: peptide ( i i i ) HYPOTHETICAL: no ( i v ) FRAGMENT TYPE: internal ( v ) PUBLICATION INFORMATION:
        ( A ) RELEVANT RESIDUES IN SEQ ID NO: From 300-306
            (without counting the first 10 amino acids which comprise the leader sequence)

( v i ) SEQUENCE DESCRIPTION: SEQ ID NO: 10:

```
Thr Ile Thr Gly Pro Gly Thr
 1               5
```

( 2 ) INFORMATION FOR SEQ ID NO:11:

( i ) SEQUENCE CHARACTERISTICS:
        ( A ) LENGTH: 20 amino acid residues
        ( B ) TYPE: amino acid
        ( C ) TOPOLOGY: linear ( i i ) MOLECULE TYPE:
        ( A ) DESCRIPTION: peptide ( i i i ) HYPOTHETICAL: no ( i v ) FRAGMENT TYPE: internal ( v ) PUBLICATION INFORMATION:
        ( A ) RELEVANT RESIDUES IN SEQ ID NO: From 307-326
            (without counting the first 10 amino acids which comprise the leader sequence)

( v i ) SEQUENCE DESCRIPTION: SEQ ID NO: 11:

```
Asn Asn Pro Glu Asn Pro Ile Thr Glu Ser Ala His Leu Asn Val
 1               5                  10                  15
Gln Cys Thr Val Ala
                 20
```

( 2 ) INFORMATION FOR SEQ ID NO:12:

( i ) SEQUENCE CHARACTERISTICS:
        ( A ) LENGTH: 20 amino acid residues
        ( B ) TYPE: amino acid
        ( C ) TOPOLOGY: linear ( i i ) MOLECULE TYPE:
        ( A ) DESCRIPTION: peptide ( i i i ) HYPOTHETICAL: no ( i v ) FRAGMENT TYPE: C-terminal ( v ) PUBLICATION INFORMATION:
( A ) RELEVANT RESIDUES IN SEQ ID NO: From 318-337
(without counting the first 10 amino acids which comprise the leader sequence)

( v i ) SEQUENCE DESCRIPTION: SEQ ID NO: 12:

His Leu Asn Val Gln Cys Thr Val Ala Glu Trp Val Leu Val Gly
 1               5                  1 0              1 5

Gln Asn Ala Thr Trp
         2 0